United States Patent [19]

Boyd et al.

[11] Patent Number: 5,510,243
[45] Date of Patent: Apr. 23, 1996

[54] MULTIPLE CHROMOGEN ENZYME TARGETING (MCET) FOR USE IN BACTERIAL CONTAMINATION MONITORING

[75] Inventors: Steven H. Boyd; Norman R. Wainwright, both of Falmouth, Mass.

[73] Assignee: Gelman Sciences, Inc., Ann Arbor, Mich.

[21] Appl. No.: 264,130

[22] Filed: Jun. 21, 1994

[51] Int. Cl.$^6$ .............................. C12Q 1/34; C12Q 1/04; C12P 39/00; C12N 1/00
[52] U.S. Cl. ..................... 435/18; 435/42; 435/34; 435/29; 435/38; 435/39; 435/14; 435/4; 435/849
[58] Field of Search .................... 435/18, 4, 34, 435/29, 7.37, 7.32, 39, 42, 41, 38, 40, 849, 14

[56] References Cited

U.S. PATENT DOCUMENTS

| | | | |
|---|---|---|---|
| 3,095,343 | 9/1960 | Berger | 156/180 |
| 3,111,702 | 7/1961 | Berger | 15/563 |
| 4,263,967 | 4/1981 | McNab et al. | 165/166 |
| 4,598,046 | 1/1986 | Kimura et al. | 435/849 |
| 4,622,297 | 11/1986 | Kappner et al. | 435/18 |
| 4,684,609 | 8/1987 | Hsu | 435/7 |
| 4,806,313 | 2/1989 | Ebersole et al. | 422/61 |
| 4,829,969 | 5/1989 | Ray | 123/557 |
| 4,868,110 | 9/1989 | Des Rosier et al. | 435/34 |
| 4,923,804 | 5/1990 | Ley et al. | 435/29 |
| 4,925,789 | 5/1990 | Edberg | 435/38 |
| 4,933,291 | 6/1990 | Daiss et al. | 436/45 |
| 5,006,462 | 4/1991 | Gattaz | 435/7.4 |
| 5,171,537 | 12/1992 | Wainwright et al. | 422/100 |
| 5,210,022 | 5/1993 | Roth et al. | 435/34 |
| 5,223,402 | 6/1993 | Abbas et al. | 435/18 |
| 5,358,854 | 10/1994 | Ferguson | 435/14 |

OTHER PUBLICATIONS

Nucleic Acids Research, vol. 13 No. 15, 1985 pp. 5457–5469.
Brenner et al, Applied & Environmental Microbiology, pp. 3534–3544, Nov. 1993.
Mamas et al, (Chem Abstract) 91: 68210 (1979).

Primary Examiner—Douglas W. Robinson
Assistant Examiner—Louise N. Leary
Attorney, Agent, or Firm—Brooks & Kushman

[57] ABSTRACT

The invention is directed to a process and a medium for simultaneous determination of the number and presence of living fecal coliform and Escherichia coli in a sample comprising 6-O-alpha-D-galactopyranosyl-D-glucose or isopropyl-beta-D-thiogalactoside as a galactosidase inducer and methyl-beta-D-glucuronide as a glucuronidase inducer. The sterile semi-solid medium also comprises non-target bacterial inhibitors, target bacterial enhancers, and multiple fluorogen and/or chromogan substrates that produce color and fluorescence upon cleavage by a specific enzyme expressed by the target bacteria in which expression is enhanced. The simultaneous detection of total coliforms via its expression of beta-galactosidase, and Escherichia coli as the target bacteria via its expression of beta-galactosidase and beta-glucuronidase is achieved rapidly and efficiently using this medium.

8 Claims, No Drawings

MULTIPLE CHROMOGEN ENZYME TARGETING (MCET) FOR USE IN BACTERIAL CONTAMINATION MONITORING

BACKGROUND OF THE INVENTION

There is a general perception that pathogenic bacteria are increasingly infecting the food supply, air supply and recreation and drinking water supply. In the last few decades, the incidence of microbial infection and water-borne disease has significantly increased worldwide. The contamination by undesirable bacteria in foodstuffs, air, and water represents a significant threat to public health. Monitoring efforts rely on conventional microbiological techniques to detect the presence of bacteria, typically including the growth of bacteria on nutrient media. The size, color and morphology of bacterial colonies are among the criteria used to identify the species present. In many cases, several different media must be employed in order to discriminate one species from another. The time necessary to carry out the many steps to achieve this result may take up to several days and require a highly trained technician. Conventional bacterial identification and confirmation techniques utilizing membrane filtration require culturing of a specimen on selective media with selection of potential colony types based on morphology and specific color, etc., to make a presumption, followed by a growth on a non-elective enrichment medium which is then transferred to a carbohydrate and pH indicator panel for confirmation. For certain membrane filtration procedures, the complete process can take several days.

In view of the increasing demand for clean water, food and air, it is essential to rapidly determine pathogen viability and growth potential prior to and after bacterialcidal treatment. Improvements are necessary in the specificity and simplicity of microbiological detection and management by developing quantitative indicators of parthenogenic bacterial viability. In recognition of the present time limitations for microbial detection, there is a need to simplify currently used methods and develop enhanced procedures for detection of viable pathogens. Current methods for determining water quality have been limited by multiple culture methods and the time required for the sampled bacteria to multiply. Efforts aimed at shortening that period have succeeded at reducing the time required from two days to as little as several hours, depending on the type of data required.

There are currently three accepted assay formats for the detection of parthenogenic bacteria in environmental samples: Multiple Tube Fermentation (MTF); Membrane Filtration (M) and Presence-Absence (PA). Based in part on technology developed in the 1920's, total and fecal coliform tests can require 24 to 72 hours to complete and rely on nonspecific bacterial biomass growth as the key indicator of fecal contamination.

Fecal coliforms are those coliform bacteria that are presumed from the feces of warm-blooded animals. Human fecal coliform bacteria which are primarily *Escherichia coli* (*E. coli*) also ferment lactose but at a higher temperature (44.5° C.). *E. coli* are commonly found in the intestinal track of humans and animals but are not usually long term inhabitants of aquatic systems. Differentiation depends on an enrichment of the medium and an elevated incubation temperature of 44.5°±0.2° C. The presence of this species is an accepted indicator of the microbiological quality of water for drinking, for recreation, as well as of food.

Several possible rapid detection procedures for *E. coli* have been described in the art. For example, isotopic fecal detection tests have been shown to required as little as one hour, see Dange, V., Jothikumar, N., Khanna, P., "One hour portable test for drinking waters" *Water Res* 22:133137, 1988; Reasoner D.J., Geldreich, E. E., "Rapid Detection of Water-borne Fecal Coliforms by $^{14}CO_2$ Release", *Mechanizing Microbiology*, Sharpe and Clark ed., 1978; Reasoner, D.J., Blannon, J.C., Geldreich, E.E., "Rapid Seven-hour Fecal Coliform Test", *Appl Environ Microbiol.*, 38:229–236, 1979. Although these procedures are specific and fast, their disadvantages include the sophistication of the instruments required as well as the use of radio-active materials.

The detection of *E. coli* from environmental samples using the DNA hybridization and more recently Polymerase Chain Reaction shows technical promise (Bej et al., "Detection of Escherichia coli and Shigella sp. in water by using the Polymerase Chain Reaction and Gene Probes for Uid", *Appl. Environ. Microbiol.*, 57(4): 1013–7, 1991). However, at present, the level of technical skill, specialized equipment and time required has dictated further development of appropriate and simpler methods.

Hydrolyzable substrates are dye moieties that are blocked in their initial condition and when cleaved during an enzyme hydrolysis step, provide chromogenic or fluorogenic signals. The determination of hydrolyric enzymes has been shown to be useful in the detection of certain species of bacteria. These methods to identify specific bacteria include the use of specific chromogenic or fluorogenic enzyme substrates and dyes, see Babb et al, U.S. Pat. No. 4,812,409; Hansen, W., Yourassowsky, E., "Detection of beta-glucuronidase in Lactose-fermenting Members of the Family Enterobacteriaceae and its Presence in Bacterial Urine Cultures", J. Clin. Micro., 20(4):1177–1179, 1984. A color change when cleaving a specific dye moiety would indicate the presence of a particular enzyme. Ideally, if there were one unique enzyme for each bacterial species of interest, one could determine its presence by monitoring the color change of the growth medium containing the substrate specific for that enzyme. This situation exists in no bacterial group described thus far, and is the focus of intense interest. It is commonly known that several bacterial species may share sets of enzymes. For example, *E. coli* produce several enzymes which may metabolize a number of substrates linked to a chromogen. However, other bacterial species (i.e., Cornybacterium, Shigella, etc.) also produce these and other enzymes. While imperfect, the use of single enzyme discrimination is permitted as part of the national primary water regulations to distinguish total and fecal coliforms (Rice, E.W., Allen, M.J., Brenner, D.J., Edberg, S.C., "Assay for beta-glucuronidase in Species of the Genus Escherichia and its Applications for Drinking-water Analysis", *Appl. Environ. Microbiol.*, 57(2): 592–3, 1991). In addition, many substrates previously proposed become yellow, which is a color difficult to distinguish from normal bacteria biomass.

SUMMARY OF THE INVENTION

The problems of the prior art have been overcome by the present invention, which provides a process for simultaneous determination of the number and presence of living fecal coliform bacterial cells. Viable coliform colony identification is accomplished by employing inhibitors and enhances to achieve minimum competition and maximum target cell growth; inducers and nutrients that maximally activate specific substrate hydrolysis and provide for rapid sustained coliform colony growth; and hydrolyzable fluorogenic and/or chromogenic substrates that can be detectable in multiple enzyme recognition format on solid supports.

More specifically, a sterile semi-solid medium is employed that comprises non-target bacterial inhibitors, target bacterial enhancers, and multiple fluorogen and/or chromogen substrates that produce color and fluorescence upon cleavage by a specific enzyme expressed by the target bacteria, which expression is enhanced. The simultaneous detection of total coliforms via its expression of β-galactosidase, and target bacteria, specifically Escherichia coli, via its expression of β-galactosidase and β-glucuronidase, is achieved rapidly and efficiently using this medium.

DETAILED DESCRIPTION OF THE INVENTION

The present invention is directed towards a process for detecting cell viability by specific enzyme amplification and detection, and addresses four basic problems:

1. Minimization of injury to living *E. coli* using membrane filter capture and physiological rinsing steps;

2. Development of a nutrient growth media that represses growth of all but the organisms of interest;

3. Induction and enhancing the rates of the specific enzyme if present; and

4. Chromatographic recognition on a solid support using indicators of specific enzyme activity that concentrate and focus the signal using both soluble and insoluble substrates and are not required for microbe growth.

By simultaneously inhibiting the growth of non-target bacteria and enhancing the growth of target bacteria, minimum competition and maximum target cell growth is achieved. This is accomplished by filtering the sample to capture the target bacteria, washing the sample with a sterile semi-solid medium containing a combination of physiological salts, buffers, surfactants, and chelating agents that selectively inhibit non-target organisms and dilute any antimicrobial activity against the target organism, which causes bacteriophage reduction and reduction in chemical and antibiotic stress, concentrates the fluorogenic and/or chromogenic signal, and allows for solid support colony recognition, as described in detail below.

The sample of interest is gently filtered onto any sterile membrane that will retain the microbe of interest. Preferably the filter has a micron pore size of from about 0.2 to about 0.45 microns. Suitable filter materials include cellulose ester, nitrocellulose, polyethylene, polysulfone and polycarbonate.

Once the bacterial cells of interest are captured on the filter, the filter is placed into contact with a semi-solid nutrient medium on a solid support. To effectively discriminate between *E. coli* and non-target bacteria, the medium includes a combination of specific sugar substrates that β-galactosidase and β-glucuronidase enzymes expressed by *E. coli* can act on. Preferably the sugars are β-D-galactoside and β-D-glucuronide having fluorogenic and/or chromogenic leaving groups bonded thereto. For example, one suitable β-galactoside sugar is 5-bromo-4-chloro-3-indoyl-β-D-galactopyrano-side (X-GAL), which results in a blue color when the chromogen is cleaved. Other suitable chromogenic/fluorogenic substrates for the enzyme galactosidase include 5-bromo-6-chloro-3-indolyl beta-D-galactopyranoside, indolyl-beta-D-galactopyranoside, 4-methylumbelliferyl-N-acetyl-beta-D-galactosaminide, 4-nitrophenyl-N-acetyl-beta-D-galactosaminide, 4-nitrophenyl-alpha-D-galactopyranoside, 2-nitrophenyl-beta-D-galactopyranoside, 4-nitrophenyl-beta-D-galactopyranoside, 5-(and-6)-carboxyumbelliferyl-beta-D-2',7'-dichlorofluorescein-di-beta-D-galactopyranoside, galactopyranoside, fluorescein-di-beta-D-galactopyranoside, resorufin-beta-D,galactopyranoside, beta-trifluoromethyl-umbelliferyl-beta-D-galactopyranoside, N-Methyl indolyl -beta-D-galactopyranoside, and 5-iodo-3-indolyl-beta-D-galactopyranoside.

One suitable β-glucuronide substrate is 4-methylumbelliferyl-β-D-glucuronide (MUG), which results in a blue color and fluoresces when the fluorogen is cleaved. Other examples 5-bromo-4-chloro-3-indoyl-beta-D-glucuronide, 3-carboxyumbelliferyl-beta-D-glucuronide, resorufin-beta-D-glucuronide, beta-trifluoromethyl-umbelliferyl-beta-D-glucuronide, 5-bromo-6-chloro-3-indolyl-beta-D-glucuronide, 6-chloro-3-indolyl-beta-D-glucuronide, indoxyl-beta-D-glucuronide, and 4-nitrophenyl-beta-D-glucuronide. Any combination of substrates may be used so long as multiple color or color/fluorescence is achieved.

Suitable solid supports for the semi-solid medium include inert pads of cellulose acetate or polyester, that may be placed in a sealed container such as a test tube, petri dish, beaker, cuvette, etc.

The semi-solid sterile medium also comprises inducers and nutrients which are employed to allow for enumeration of coliform colonies and the enhanced expression of β-galactosidase and β-glucuronidase for the detection of *E. coli*, if present. The media includes a combination of nutrients, buffers, inhibitors, fungicides, virasides, etc. to inhibit growth of non-target bacteria and sufficiently grow and form colonies of target bacteria visible to the eye. Maximum activation of specific substrate hydrolysis and rapid sustained coliform colony growth is achieved.

Suitable nutrient salts include NaCl, KCl, $(NH_4)_2SO_4$, $MgSO_4$. Suitable nutrients include meat peptone, yeast extract, casein (acid hydrolysate) glucose soluble starch sodium pyruvate and agar. Suitable nutrient buffers include $NaH_2PO_4$, $KH_2PO_4$, tris(hydroxymethyl)-aminomethane hydrochloride and tris(hydroxymethyl)-aminomethane. Suitable microbiological inhibitors include methyl-1-(butylcaramoyl)-2-benzimidazolecarbamate and benzylpenicillin (sodium salt).

Antibiotics or combinations of antibiotics are incorporated into the medium to suppress growth of non-target bacteria. Preferred bacterial antibiotics include vancomycin, movomycin, polymyxin B and colistin.

Fungi, such as yeast and other environmentally abundant molds may also overgrow the target species, thereby interfering with growth and enumeration. Minimal levels of fungicides may be included in the medium to suppress such growth. Examples include amphotericin B, nystatin and fungizone.

Bacteriophage contamination present in the sample may also selectively inhibit susceptible species. Also, conditions that favor bacteriophage adsorption are minimized while surfactants and chelating agents can be included in the media to interfere with phage attachment. Such reagents can be present in an amount ranging from 0,001 to 0.1% by weight and include TRITON, TWEEN, polyethylene glycol, EGTA, EDTA and citrate.

Suitable galactosidase inducers present in the media include 6-O-α-D-Galactopyranosyl-D-glucose and isopropyl-β-D-thiogalactoside (IPTG). A suitable glucuronidase inducer present in the media is methyl-β-D-Glucuronide(sodium salt). The pH of the media should be maintained at about 7.4±0.5. Table 1 below gives examples of the various medium components, including preferred amounts and operative amounts.

TABLE 1

| Component | Amount (g/l) | |
|---|---|---|
| | Preferred | Range |
| Nutrient Salts | | |
| Sodium chloride | 8.0 | 2.0–20.0 |
| Potassium chloride | 0.2 | 0.05–1.0 |
| Ammonium sulfate | 1.0 | 0.25–2.5 |
| Magnesium sulfate | 0.001 | 0–0.1 |
| Substrates | | |
| 5-bromo-4-chloro-3-indolyl-β-D-galactopyranoside (X-GAL) | 0.25 | 0.02–1.5 |
| 4-methylumbelliferyl-β-D-glucuronide (MUG) | 0.1 | 0.01–0.3 |
| Galactosidase Inducers | | |
| 6-O-α-D-galactopyranosyl-D-glucose | 0.25 | 0.02–2.5 |
| Isopropyl-β-D-thiogalactoside | 0.004 | 0.0004–1.5 |
| Glucuronidase Inducer | | |
| Methyl-β-D-glucuronide | 0.005 | 0.0005–1.2 |
| Microbiological Inhibitors | | |
| Methyl 1-(butylcaramoyl)-2-benzimidazolecarbamate | 0.001 | 0.0001–0.01 |
| Benzylpenicillin (Na salt) | 0.001 | 0.0001–0.01 |
| Nutrient Buffers | | |
| Sodium phosphate | 1.44 | 0.1–3.5 |
| Potassium phosphate | 0.24 | 0.02–0.5 |
| Tris(hydroxymethyl)-amino methane (hydrochloride) | 6.61 | 0.5–15.0 |
| Tris(hydroxymethyl)-aminomethane | 0.97 | 0.01–3.25 |
| Nutrients | | |
| Meat peptone | 0.1 | 0.01–0.5 |
| Yeast extract | 0.1 | 0.01–0.5 |
| Casein, acid hydrolysate | 0.1 | 0.01–0.5 |
| Glucose | 0.1 | 0.01–0.5 |
| Soluble starch | 0.1 | 0.01–0.5 |
| Sodium pyruvate | 0.06 | 0.001–0.6 |
| Agar | 1.0 | 0.1–0.5 |

EXAMPLE 1

Detection and Recovery of E. coli in Seawater

Seawater samples (100 ml) were taken from the waters of Woods Hole, Massachusetts, having a salinity of 30 0/00 and sterile filtered with a 0.2 μ pore size filter (47 mm, GN-6, available from Gelman Sciences) using a standard vacuum filter manifold. Control samples using sterile 0.9% saline and replicate seawater tests were spike with E. coli (ATCC) at 8 and 80 cells per sample (±20%) and filtered. Each filter was washed with 10 ml. of a solution consisting of a medium containing peptone solution (0.5%), TWEEN-20 (0.01%) in PBS pH 7.4. Following the wash, the filters were transferred to sterile petri dishes containing 2.5 ml of a semisolid gel media having the combination of the nutrients, inducers, inhibitors and buffers described in Table 1 in the preferred amounts shown therein, with 200 μg/ml β-galactosidase substrate 5-bromo-6-chloro-3-indolyl-β-D-galactopyranoside, and 50 μg/ml β-glucuronidase substrate trifluororm-ethyumbelliferal-β-D-glucuronide. Samples were incubated at 35° C.±0.1° C. for 24 hours.

Control samples of both sterile saline and seawater containing no E. coli showed no growth. Samples spiked with both low and high numbers of E. coli had growth of bacterial colonies on the filter appearing magenta in white light, indicating metabolism of the galactosidase substrate. Under ultraviolet light (312–366 nm), the colonies had a fluorescent yellow-green halo, indicating metabolism of the glucuronidase substrate.

EXAMPLE 2

Chlorinated Tap Water Comparison

Finished tap water (100 ml) containing 0.7–1.1 ppm chlorine and having no detectable E. coli growth (M-FC Membrane filter technique) was spiked with 40 (±8) colony forming units (cfu) E. coli (ATCC) and filtered by standard membrane filter techniques using a Gelman GN-6 membrane as in Example 1. A control solution of distilled water was similarly spike with the same number of E. coli. β-glucuronidase substrate 4-methylumbelliferyl-β-D-glucuronide, and β-galactosidase substrate 5-bromo-4-chloro-3-indolyl-β-D-galactopyranoside were included with nutrients, inducers, inhibitors and buffers as listed in Table 1 in the preferred amounts shown therein, and 2.5 ml added to an absorbent pad. The filter was placed on the pad and incubated at 37° C. for 24 hours. The colonies of E. coli were visible and colored blue in white light, from the metabolism of the galactosidase substrate, and appeared with a blue, fluorescent halo when illuminated with an ultraviolet light (312–366 nm), indicating metabolism of the glucuronidase substrate. Bacterial exposed to chlorinated tap water showed no significant difference in number and size compared to those exposed to distilled water.

Example 3

Multiple Species Detection

Since the purpose of this medium is to enumerate E. coli as well as discriminate them from other coliform bacteria (Escherichia sp., Enterobacter sp., Citrobacter sp., and Klebsiella sp.), a mixed culture experiment was performed. Approximately 40 cfu of E. coli (ATCC 11229, ATCC 8739) were plated separately or mixed with one of the following species: Klebsiella pneumoniae (ATCC 13883), *Citrobacter freundii* (GMCC 55), Enterobacter aerogenes (EPA strain ATCC 49701), Enterobacter aerogenes (ATCC 8427), *Pseudomonas aeruginosa* (ATCC 13048), *Pseudomonas aeruginosa* (ATCC 14207) or Proteus vulgaris (ATCC 8427).

Dilutions of individual and mixed species were prepared in 0.9% sterile saline and subjected to standard filtration techniques. Filters were incubated with the medium a shown in Table 1 using the preferred amounts listed therein, and containing β-glucuronidase substrate4-methylumbelliferyl-β-D-glucuronide, and β-galactosidase substrate 5-bromo-4-chloro-3-indolyl-β-D-galactopyranoside. After incubation at 37° C. for 24 hours, colonies were inspected for color in white light and fluorescence under ultraviolet light (312–366 nm).

Colonies which appear blue and fluoresce under ultraviolet light are considered E. coli. All non-E. coli coliforms appear as blue colonies in white light with no fluorescence under ultraviolet light. There was some autofluorescence noticed with P. aeruginosa, but a true colony was not present. To confirm autofluorescence, ultraviolet light is directed from the back of the petri dish. True E. coli fluorescence is evident from either side, whereas P. aeruginosa is only seem from the top. All E. coli/other coliform combination was able to be unambiguously discriminated.

What is claimed is:

1. A rapid method for the simultaneous detection of total coliforms and *Escherichia coli* in a sample, comprising:

filtering the sample to capture total coliforms and *Escherichia coli* present in said sample;

preparing a medium comprising a non-target bacteria inhibitor, 6-O-alpha-D-galactopyranosyl-D-glucose or isopropyl-beta-D-thiogalactoside as the inducer for β-galactosidase, a fluorogenic or chromogenic substrate for said β-galactosidase, methyl-beta-D-glucuronide as the inducer for β-glucuronidase, and a fluorogenic or chromogenic substrate for said β-glucuronidase;

contacting said filtered sample with said medium;

incubating said medium to produce colonies of said total coliforms and *Escherichia coli*;

detecting and correlating the signal produced by said fluorogenic or chromogenic substrate for said β-galactosidase to total coliforms present in said sample; and detecting and correlating the signal produced by said fluorogenic or chromogenic substrate for said β-glucuronidase to the presence of *Escherichia coli* in said sample.

2. The method of claim 1, wherein the presence of Escherichia coli is detected by exposing said sample to UV light.

3. The method of claim 1, wherein said medium further comprises one or more *Escherichia coli* nutrients selected from the group consisting of meat peptone, yeast extract, casein, glucose, soluble starch, sodium pyruvate and agar.

4. The method of claim 3, wherein said medium further comprises an amount of a non-target bacteria inhibitor effective to render any competing non-target bacteria present in said sample unable to metabolize said chromogenic or fluorogenic substrate.

5. The method of claim 1, further comprising enumerating said detected *Escherichia coli*.

6. A medium for the simultaneous detection of total coliforms and *Escherichia coli* in a sample, comprising:

(a) an amount of a non-target bacteria inhibitor effective to inhibit growth of non-target bacteria;

(b) an amount of 6-O-alpha-D-galactopyranosyl-D-glucose or isopropyl-beta-D-thiogalactoside as the inducer for the enzyme β-galactosidase effective to enhance expression of β-galactosidase by coliforms;

(c) an amount of methyl-beta-D-glucuronide as the inducer for the enzyme β-glucurondidase effective to enhance expression of β-glucuronidase by *Escherichia coli*;

(d) a fluorogenic or chromogenic first substrate capable of being metabolized by β-glactosidase produced by coliform bacteria and *Escherichia coli*, in an amount effective to allow colony recognition by the presence of a first color;

a fluorogenic or chromogenic second substrate capable of being metabolized by β-glucuronidase produced by *Escherichia coli*, in an amount effective to allow colony recognition by the presence of a second color;

wherein said first color and said second color are not the same.

7. The medium of claim 6, further comprising one or more Escherichia coli nutrients selected from the group consisting of meat peptone, yeast extract, casein, glucose, soluble starch, sodium pyruvate and agar.

8. The medium of claim 6, further comprising an amount of a non-target bacteria inhibitor effective to render any competing non-target bacteria present in said sample unable to metabolize said chromogenic or fluorogenic substrate.

* * * * *

UNITED STATES PATENT AND TRADEMARK OFFICE
CERTIFICATE OF CORRECTION

PATENT NO. : 5,510,243
DATED : April 23, 1996
INVENTOR(S) : Steven H. Boyd, Norman R. Wainwright It is certified that error appears in the above-indentified patent and that said Letters Patent is hereby corrected as shown below:

In Column 2, line 1, after "to", replace "required" with --require--.

In Column 5, line 51, after "were", replace "spike" with --spiked--.

In Column 6, line 16, after "similarly", replace "spike" with --spiked--.

In Column 6, line 28, after "substrate.", replace "Bacterial" with --Bacteria--.

In Column 6, line 50, after "medium", replace "a" with --as--.

Signed and Sealed this

First Day of October, 1996

Attest:

BRUCE LEHMAN

*Attesting Officer*  *Commissioner of Patents and Trademarks*